United States Patent [19]
Lazzari

[11] Patent Number: 6,060,089
[45] Date of Patent: May 9, 2000

[54] PRODUCT BASED ON POLYSACCHARIDES FROM BAKERS' YEAST AND ITS USE AS A TECHNOLOGICAL COADJUVANT FOR BAKERY PRODUCTS

[75] Inventor: Fabrizio Lazzari, Parma, Italy

[73] Assignee: Farmint Group Holding S.A., Luxembourg

[21] Appl. No.: 09/288,571

[22] Filed: Apr. 9, 1999

[30] Foreign Application Priority Data

Apr. 17, 1998 [EP] European Pat. Off. ............. 98201232

[51] Int. Cl.⁷ ................... C12N 1/06; C12N 1/18; A21D 8/04; A21D 2/34; A23J 1/18
[52] U.S. Cl. ............. 426/19; 426/656; 536/123.12; 435/255.2; 435/259
[58] Field of Search .................. 435/71.1, 101, 435/255.2, 255.21, 259; 536/123.12; 426/19, 549, 656, 658

[56] References Cited

U.S. PATENT DOCUMENTS

| | | | |
|---|---|---|---|
| 3,867,554 | 2/1975 | Sucher et al. ............... | 426/60 |
| 3,888,839 | 6/1975 | Newell et al. ............... | 260/112 |
| 5,082,936 | 1/1992 | Jamas et al. ............... | 536/123 |
| 5,085,875 | 2/1992 | Penttila et al. ............. | 426/62 |
| 5,385,832 | 1/1995 | Tuse et al. ................. | 435/101 |

FOREIGN PATENT DOCUMENTS

| | | |
|---|---|---|
| 0 515 216 A2 | 5/1992 | European Pat. Off. . |
| 0 556 347 A2 | 4/1993 | European Pat. Off. . |
| WO 91/03495 | 3/1991 | WIPO . |

OTHER PUBLICATIONS

Manners et al., *Biochem. J.*, vol. 135, pp. 11–36, 1973.

*Primary Examiner*—Keith D. Hendricks
*Attorney, Agent, or Firm*—Nixon & Vanderhye P.C.

[57] ABSTRACT

The invention relates to a product derived from bakers' yeast and containing from 45% to 60% by weight of polysaccharides (glucans and mannans), from 35% to 45% by weight of proteins, short-chain peptides and amino-acids, and from 3% to 5% by weight of nucleic acids and nucleotides, to a method for its preparation, and to the use of the product as a technological coadjuvant for dough for bread and other bakery products.

11 Claims, No Drawings

PRODUCT BASED ON POLYSACCHARIDES FROM BAKERS' YEAST AND ITS USE AS A TECHNOLOGICAL COADJUVANT FOR BAKERY PRODUCTS

FIELD OF THE INVENTION

The present invention relates in general to a product based on polysaccharides of the glucan and mannan classes and to a method of obtaining this product from yeasts and/or fungi.

In particular, the invention relates to a product based on beta-polysaccharides obtained from bakers' yeast (*Saccharomyces cerevisiae*) and to the use of this product as a technological coadjuvant in the production of bread and other bakery products.

BACKGROUND ART

It is known that the saccharide component of the cell walls of yeasts and fungi is constituted mainly by glucans and mannans; the polysaccharides which can be obtained from *Saccharomyces cerevisiae* are of particular interest in the food field since this micro-organism has been used by man in food for centuries and therefore offers the best guarantee of being harmless.

The cell walls of *Saccharomyces cerevisiae* are composed mainly of glucan which in turn is constituted by a main chain of glucose units joined by $B(1-3)$ glucoside bonds with a low degree of inter- and intramolecular branching by means of $B(1-6)$ glucoside bonds.

The polysaccharides contained in the walls of *Saccharomyces cerevisiae* can be obtained with a high degree of purity by various methods such as, for example, those described in U.S. Pat. Nos. 5,082,936 and 3,867,554 and in Italian patent application MI96A000681.

The use of these substances as thickeners for food preparations such as creams, ices, sauces, etc. has been proposed because of their ability to absorb and retain large quantities of water and to increase viscosity. Moreover, when added to substantially liquid food products, they cause these products to produce a sensation of a fatty consistency when tasted, even though these polysaccharides are substantially fat free.

SUMMARY OF THE INVENTION

The problem upon which the present invention is based is that of providing a product which is based on the aforementioned polysaccharides and which is particularly suitable for use as a technological adjuvant in the preparation of bakery products such as bread, biscuits, brioches and the like.

This problem has been solved by a product derived from bakers' yeast and containing from 45% to 60% by weight of polysaccharides (glucans and mannans), from 35% to 45% by weight of proteins, short-chain peptides and amino-acids, and from 3% to 5% by weight of nucleic acids and nucleotides.

Another object of the present invention is a method for producing the above mentioned product.

DETAILED DESCRIPTION OF THE INVENTION

The present invention relates to a product derived from bakers' yeast and containing from 45% to 60% by weight of polysaccharides (glucans and mannans), from 35% to 45% by weight of proteins, short-chain peptides and amino-acids, and from 3% to 5% by weight of nucleic acids and nucleotides.

The aforementioned product can be produced by a method which comprises the steps of:

preparing a suspension of *Saccharomyces cerevisiae* yeast in a 0.1–0.3N solution of a strong acid to give a solids content of 20–25% and a pH of from 2 to 5, maintaining stirring at 75–80° C. for 30–90'.

separating the solid component from the suspension, resuspending the solid component in a 25–30% NaCl solution to give a solids content of 25–30% and leaving it to rest for 12–15 hours, separating the solid component and washing it with water, resuspending the solid component in a 0.1–0.3N alkaline hydroxide solution to give a solids content of 25–30%, maintaining stirring at 75–80° C. for 30–90'.

neutralizing with concentrated HCl and recovering the solid component by separating it from the supernatant liquid, drying the solid component to give the product.

The strong acid is preferably hydrochloric acid and the alkaline hydroxide is preferably sodium hydroxide.

The above-mentioned steps for separating the solid component are carried out by centrifuging or, preferably, by filtration.

The moisture content of the product is generally between 0.1 and 1%.

The protein content of the product is generally between 15 and 20%.

The extraction of the polysaccharides from the cell wall of bakers' yeast by this method produces a product based on polysaccharides of the glucan and mannan classes but also comprising other components, particularly amino-acids, nucleic acids and nucleotides.

A product of this type is particularly suitable for use as a technological coadjuvant in the production of bread and other bakery products since, when it is added to the starting dough, it improves the organoleptic characteristics, the volume, the softness and the preservability of the final bakery product.

When the product obtained by the method according to the invention is added to dough for bakery products in quantities variable from 0.5 to 5 by weight relative to the weight of the dough, the polysaccharides contained therein have a bioabsorbent effect with respect to water, retaining it for a long time and rendering it unavailable for the mass growth of micro-organisms or for the growth of small microbial populations which lead to an alteration in the organoleptic properties of the final bakery product.

The prolonged water retention within the bakery products considerably slows the hardening process in these products, lengthening their shelf-life.

The non-availability of the water, which is proved by the low Aw value of the bakery products to which the product of the invention has been added, prevents or at least hinders the growth of bacteria and other micro-organisms, keeping the microbiological purity of the product as well as its organoleptic properties unchanged for a long time.

Moreover, the latter properties are enhanced by the presence of a significant content of amino-acids, nucleic acids and nucleotides within the product according to the invention.

It has been found that the presence of these components alongside the polysaccharides does not lead to any problems either from the point of view of the workability of the dough or from the point of view of the microbiological purity and preservability of the final bakery products but, on the contrary, leads to a considerable improvement in their organoleptic characteristics.

Further advantages of the product according to the invention will become clear from the non-limiting examples given below.

EXAMPLE 1

10 kg of lyophilized live bakers' yeast (*Saccharomyces cerevisiae*) was suspended with 30 litres of a 0.2N HCl solution giving a suspension with a solids content of 25% and a pH of 4.3.

The suspension was heated to 78° C. with stirring for 60', was cooled to ambient temperature, and was filtered with a porous plate filter in order to separate the solid component from the liquid component.

The solid component was resuspended with 30 litres of 25% NaCl and left to rest for 15 hours. The suspension was then re-filtered to remove the supernatant liquid. The residue was washed with water to achieve a negative chloride reaction in the washing water.

The residue was then resuspended with 30 litres of a 0.2N NaOH solution (final solids content about 25%) and the resulting suspension was kept at 75° C. for 30' with stirring.

After cooling to ambient temperature, the suspension was neutralized with 37% HCl and filtered to remove the supernatant liquid.

The residue was washed with water and resuspended in water to give a suspension with a 40% solids content which, finally, was dried by a drum drier. The final product was in the form of a powder having characteristic colour, odour and flavour similar to those of bakers' yeast. The moisture content of the product was approximately 0.5% and its water activity was less than 0.4.

Chemical analysis of the product revealed the presence of a polysaccharides content (glucans and mannans) of 47%, a nitrogenous compounds content of 42% (including about 16.5% of proteins, about 18.5% of short-chain peptides and amino-acids, and about 5% of nucleotides and nucleic acids), a total chlorides content (expressed as NaCl) of 5.5%, 2.5% of lipids, and 3.0% of ash.

When the test conditions of the method were varied within the ranges indicated above, the polysaccharides content of the final product varied from 45% to 60% by weight, the protein content varied from 15 to 20%, the peptides and amino-acids content varied from 16 and 22%, and the nucleic acids and nucleotides content varied between 3 and 5%.

EXAMPLE 2

Type OO wheat flour was mixed with water, salt and bakers' yeast in the usual proportions (water:flour ratio by weight 1:1) and with a quantity of the product obtained in accordance with Example 1 equal to 1% of the total weight of the dough (dough A).

In parallel, a dough (dough B) was prepared from the same quantities of flour, water, salt and bakers' yeast, without the addition of the product.

The two doughs were then passed through a drum roller, divided up, formed into rolls and transferred to a rising chamber at 28–30° C. in conditions of high humidity. Upon completion of the rising, the rolls were weighed and baked in an oven at about 230° C. for 12 minutes. After cooling to ambient temperature, the rolls were weighed again.

An organoleptic evaluation of the rolls produced from the two doughs A and B was carried out by a panel of tasters. The crusts of the rolls produced with both doughs were judged homogeneous, friable and of characteristic colour; the soft parts of both types of bread were elastic and of uniform porosity.

The odour and flavour of the rolls produced from dough A were judged very pleasant and decidedly more pronounced than the odour and flavour of the rolls produced from dough B.

Other marked differences between the rolls produced with the two doughs consisted of the specific volume which was 10% greater for the rolls produced with dough A, and of the Stevens consistency of the crust which, initially, was similar for the rolls produced from both doughs but, after 36–48 hours, was decidedly better for the rolls produced from dough A.

The rolls produced from dough A showed a lower weight loss after baking.

The rolls produced from the two doughs A and B were subjected to a test of preservability at ambient temperature.

The times taken by the rolls to harden was evaluated by organoleptic tests carried out by panels of tasters. The rolls produced from dough A showed a hardening time approximately 5 times longer than that of the comparison rolls.

Finally, the time required for a fungal contamination to appear in the two types of rolls after they had been kept in a moist atmosphere at 25–27° C. was evaluated; the fungal contamination started to appear after 36 hours in the rolls produced from dough B, whereas, for the rolls produced from dough A, the start of contamination was noticed only after 72 hours.

COMPARISON EXAMPLE

Type OO wheat flour was mixed with water, salt and baker's yeast in the usual proportions (water:flour ratio by weight 1:1) and with a quantity of a standard beta-glucan (Laminarin from Sigma Chemical Company) equal to 1% of the total weight of the dough (dough C).

The dough thus produced was subjected to the same processing as described in Example 1 producing, upon completion, rolls which were weighed, baked in an oven at about 230° C. for 12 minutes, and re-weighed after cooling to ambient temperature.

Organoleptic evaluation of the rolls produced from dough C in comparison with the rolls produced from dough A of Example 1 was carried out by a panel of tasters.

The crusts of the rolls produced from dough C were judged less friable than those of the rolls produced with dough A.

The odour and flavour of the rolls produced from dough A were judged to be decidedly more pronounced than the odour and flavour of the rolls produced from dough C. Only the weight loss with baking was lower for the rolls produced from dough C than that observed for the rolls produced with dough A.

The preservability characteristics (hardening time, resistance to fungal contamination) were very similar for rolls of both types.

In conclusion, when the product according to the present invention was used as a technological coadjuvant in the production of bread and other bakery products, it showed substantially the same properties as those conferred by a pure polysaccharide in terms of preservability and, at the same time, brought about an enhancement of the organoleptic properties typical of bakery products which does not occur with the use of a pure polysaccharide.

What I claim is:

1. A product derived from bakers' yeast comprising from 45% to 60% by weight of polysaccharides, from 35% to 45% by weight of proteins, short-chain peptides and amino-acids, and from 3% to 5% by weight of nucleic acids and nucleotides.

2. A method for making a product derived from bakers' yeast which comprises the steps of:

(a) preparing a suspension of *Saccaromyces cerevisiae* yeast in a 0.1–0.3N solution of a strong acid to give a solids content of 20–25% and a pH of from 2 to 5, (b) maintaining stirring at 75–80° C. for 30–90 minutes, (c) separating the solid component from the suspension, (d) resuspending the solid component in a 25–30% NaCl solution for 12–15 hours to give a solids content of 25–30%, (e) separating the solid component and washing it with water, (f) resuspending the solid component in a 0.1–0.3 alkaline hydroxide solution to give a solids content of 25–30%, (g) maintaining stirring at 75–80° C. for 30–90 minutes, (h) neutralizing with concentrated HCl and recovering the solid component by separating it from the supernatant liquid, and (i) drying the solid component to obtain the product.

3. A method according to claim 2, in which the strong acid is hydrochloric acid and the alkaline hydroxide is sodium hydroxide.

4. A method according to claim 3, wherein steps (c) and (e) are practiced by centrifuging or filtration.

5. A method according to claim 2, wherein step (i) is practiced to obtain a product having a moisture content of between 0.1% and 1%.

6. A method according to claim 3, wherein step (i) is practiced to obtain a product having a moisture content of between 0.1% and 1%.

7. A method according to claim 4, wherein step (i) is practiced to obtain a product having a moisture content of between 0.1% and 1%.

8. Dough for bread and other bakery products which comprises, as a technological coadjuvant for the dough, a product according to claim 1.

9. Dough according to claim 8, wherein the product is present in an amount from 0.5% to 5% by weight relative to the weight of the dough.

10. A product according to claim 1, wherein the product has a moisture content between 0.1% and 1%.

11. A product according to claim 1, wherein the polysaccharides are glucans or mannans.

* * * * *